United States Patent [19]
Boaz

[11] Patent Number: 5,777,164
[45] Date of Patent: Jul. 7, 1998

[54] PROCESS FOR THE PREPARATION OF HIGH PURITY O-SUBSTITUTED HYDROXYLAMINE DERIVATIVES

[75] Inventor: Neil Warren Boaz, Kingsport, Tenn.

[73] Assignee: Eastman Chemical Company, Kingsport, Tenn.

[21] Appl. No.: 837,134

[22] Filed: Apr. 14, 1997

[51] Int. Cl.⁶ .................... C07C 239/20; C07C 259/00; C07C 259/06; C07C 259/10
[52] U.S. Cl. .................... 564/301; 560/312; 560/315; 562/621; 562/622; 564/300
[58] Field of Search .................... 560/312, 315; 562/621, 622; 564/300, 301

[56] References Cited

U.S. PATENT DOCUMENTS

| | | | |
|---|---|---|---|
| 3,190,800 | 6/1965 | Furst | 560/312 |
| 4,965,390 | 10/1990 | Schneider | 558/7 |
| 4,981,996 | 1/1991 | Wyss et al. | 564/301 |
| 5,206,406 | 4/1993 | Lee | 564/301 |
| 5,557,013 | 9/1996 | Keil et al. | 564/301 |

FOREIGN PATENT DOCUMENTS

| | | |
|---|---|---|
| 0 121 701 | 10/1984 | European Pat. Off. |
| 0 158 159 | 10/1985 | European Pat. Off. |
| 0 259 850 | 3/1988 | European Pat. Off. |
| 29 27 117 | 1/1981 | Germany |
| 3615473 | 3/1988 | Germany |
| 05163228 | 6/1993 | Japan |
| 9504032 | 7/1994 | WIPO |

OTHER PUBLICATIONS

Brady, O. L.; Peakin, F. H. *J. Chem. Soc.* 1930, 226.
Cooley, J. H.; Bills, W. D.; Throckmorton, J. R. *J. Org. Chem.* 1960, 25, 1734.
Fishbein, W. N.; Daly, J.; Streeter, C. L. *Anal. Biochem.* 1969, 28;.
Shatzmiller, S.; Bercovici, S. *Leibigs Ann. Chem.* 1992, 997.
Fuller, A. T.; King, H. J. *J. Chem. Soc.* 1947, 963.
Tiecco, M.; Testaferri, L.; Tingoli, M.; Marini, F. *J. Chem. Soc., Chem. Commun.* 1995, 237.

*Primary Examiner*—Peter O'Sullivan
*Attorney, Agent, or Firm*—Karen A. Harding; Harry J. Gwinnell

[57] ABSTRACT

The present invention discloses a method comprising the steps of:

a) forming in an aqueous solution a hydroxamic acid from a hydroxylamine free base and anhydride having the formula $(RCO)_2O$ wherein R is H or a substituted or unsubstituted $C_{2-6}$ alkyl, $C_{2-6}$ alkenyl, $C_{6-10}$ aryl, or $C_{4-10}$ heteroaryl; and b) treating said hydroxamic acid with an alkylating agent in the presence of at least one proton scavenger under conditions sufficient to consume substantially all of said alkylating agent to form an O-substituted hydroxamate.

The protection and alkylation are readily effected in water (with no alcohol co-solvent) without the need for phase-transfer catalysis and with little hydrolysis of the alkylating agent.

9 Claims, No Drawings

PROCESS FOR THE PREPARATION OF HIGH PURITY O-SUBSTITUTED HYDROXYLAMINE DERIVATIVES

INTRODUCTION

O-substituted hydroxylamine derivatives are of particular interest to the agrochemical field, mainly due to their widespread use as synthetic components of numerous herbicides. There are a wide variety of these species, differing in the substituent on the oxygen. More efficient methods for the preparation of these materials in high purity are of great interest.

PRIOR ART

There have been numerous strategies used to generate O-substituted hydroxylamine derivatives, but most follow the same general pattern: hydroxylamine nitrogen protection, derivatization of the oxygen, then removal of the protecting group. The protecting groups have varied from oximes (e.g., acetone oxime) as disclosed by Ger. Offen. DE 29 27 117, EP A 0 259 850, EP A 0 158 159, EP A 0,121,701 and WO 9504032, to imides as disclosed by Ger. Offen. DE 3 615 473, to hydroximic acid esters as disclosed by U.S. Pat. No. 4,965,390, to hydroxamic acids as disclosed by JP 05163228 (Kokai); Brady, O. L.; Peakin, F. H. *J. Chem. Soc.* 1930, 226; Cooley, J. H.; Bills, W. D.; Throckmorton, J. R. *J. Org. Chem.* 1960, 25, 1734; Yale, H. L. *Chem. Rev.* 1943, 33, 209; Fishbein, W. N.; Daly, J.; Streeter, C. L. *Anal. Biochem.* 1969, 28; Shatzmiller, S.; Bercovici, S. *Leibigs Ann. Chem.* 1992, 997; Fuller, A. T.; King, H. *J. Chem. Soc.* 1947, 963. Of the latter, the initial hydroxamic acid is usually prepared by mixing the desired acid derivative (usually an ester) with a hydroxylamine salt and a metal alkoxide or hydroxide in a mixture of a lower alcohol and water. Subsequent alkylation of the oxygen affords the O-substituted hydroxamate. This alkylation is most often performed in a lower alcohol or an alcohol/water mixture with alkoxide, hydroxide, or carbonate as base. Reaction times are often extended.

Other alkylation methodologies include performing the alkylation in THF with sodium hydride as base as disclosed in Tiecco, M.; Testaferri, L.; Tingoli, M.; Marini, F. *J. Chem. Soc., Chem. Commun.* 1995, 237. Removal of the acyl group from the nitrogen produces the O-substituted hydroxylamine.

DESCRIPTION OF THE INVENTION

This invention pertains to a method for the preparation in high purity of O-substituted hydroxylamine derivatives comprising the steps of:

a) forming a hydroxamic acid from hydroxylamine free base and an acid anhydride in an aqueous solution; and b) treating said hydroxamic acid in water without a co-solvent with an alkylating agent in the presence of at least one proton scavenger under conditions sufficient to consume substantially all of said alkylating agent to form O-(alkyl) hydroxamate.

The present invention further comprises purification of the hydroxamate and removal of the acyl protecting group.

Unlike previous work, all steps are performed in water using hydroxide as base with no alcohol co-solvent. This greatly simplifies the process, since there is no lower alcohol to complicate product isolation.

In addition, the totally aqueous process allows the formation of the O-substituted hydroxamate in one pot with no need to isolate the hydroxamic acid as was required by the prior art processes. The aqueous process also allows reduced reaction volumes and affords a surprisingly rapid and clean alkylation step with minimal hydrolysis of the alkylating agent and with no need for phase-transfer catalysis.

This invention also pertains to a novel deacylation comprising the steps of acyl group recycling through an exchange reaction between the O-substituted hydroxamate and hydroxylamine to produce O-substituted hydroxylamine and regenerating the initial hydroxamic acid intermediate.

In the first step of the present invention hydroxylamine is reacted with at least one acid anhydride. The hydroxylamine free base may be purchased or formed from a hydroxylamine acid addition salt by the action of base. Suitable bases included sodium hydroxide, potassium hydroxide, potassium carbonate and the like. The acid anhydride is selected from anhydrides having the formula $(RCO)_2O$ wherein R is H or a substituted or unsubstituted $C_{2-6}$ alkyl, C2–6 alkenyl, $C_{6-10}$ aryl, or $C_{4-10}$ heteroaryl group. Suitable substituents on the R groups are selected from halide, alkoxy, alkylthio, ester, ketone and mixtures thereof.

Without isolation, the aqueous hydroxamic acid thus formed is treated with an alkylating agent and a proton scavenger. Suitable alkylating agents have the formula $R'CH_2X$ wherein X is selected from Cl, Br, I, $OSO_2R''$ and R' and R" are independently selected from substituted or unsubstituted $C_{2-6}$ alkyl, C2–6 alkenyl, $C_{6-10}$ aryl, or $C_{4-10}$ heteroaryl. Suitable substituents are selected from halide, alkoxy, alkylthio, ester, and ketone. An example of a suitable alkylating agent is E-1,3-dichloropropene (DCP). Suitable proton scavengers are selected from alkali and alkaline earth metal hydroxides and carbonates.

The hydroxamic acid reaction mixture is heated to a temperature between about 50° and about 100° C. for a time sufficient to substantially consume the alkylating agent according to GC analysis. Preferably the temperature is about 65° C. Preferably the time is from about 1 to about 24 hours, and more preferably is about 3 hours.

The hydroxamic acid formation and alkylation is performed completely in aqueous solution. Suprisingly, only small quantities of the alkylating agent (<3%) are hydrolyzed. The presence of a phase-transfer catalyst had no effect on the rate of the reaction, which was also surprising since the reaction mixture was biphasic (alkylating agent and water are not miscible).

The product hydroxamate 1 along with small amounts of impurities are readily separated from the aqueous reaction mixture. The intermediate may be purified as its salt (2) by extraction into aqueous base having a pH of 12 or greater. Preferred bases include sodium hydroxide, potassium hydroxide, calcium hydroxide, and barium hydroxide, with sodium hydroxide being most preferred. A single extraction from an organic solution removed more than 99% of 1 according to GC analysis, while leaving the impurities in the organic solution (FIG. 1).

FIG. 1

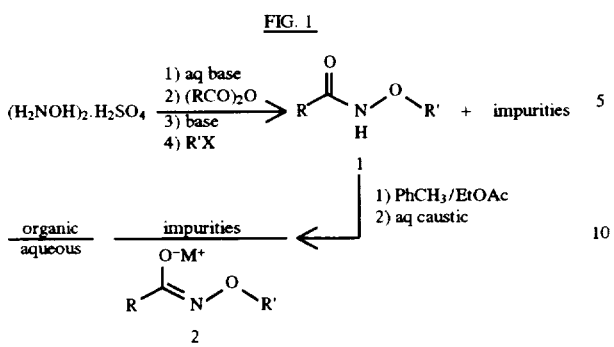

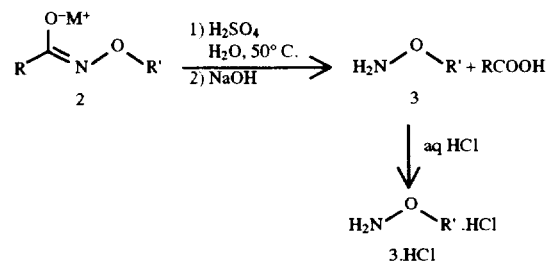

The removal of the acyl protecting group may be effected in two ways. First, the intermediate 1 may be reacted with hydroxylamine free base (itself generated from the salt 2 and hydroxylamine sulfate) at a temperature between about 50° C. and about 100° C. until the desired conversion is reached. Generally times of about one to about 12 hours are sufficient. Those of skill in the art will appreciate that higher reaction temperatures will require shorter reaction times. Preferably the reaction is conducted at about 65° C. for about 8 hours. This reaction resulted in an acyl exchange reaction between the two hydroxylamine moieties, affording the free base 3 of the desired product and the hydroxamic acid, the latter ready for recycle, as shown below.

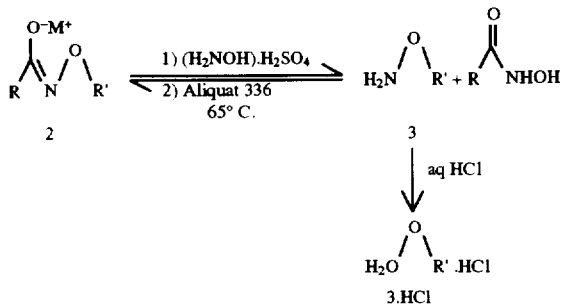

This exchange reaction is an equilibrium process, and affords about 80% conversion to the desired product. Both the residual intermediate and the generated hydroxamic acid can be readily recycled, while the final product can be isolated as an aqueous solution of an acid addition salt.

Alternatively, the aqueous solution of 2 is hydrolyzed under acidic conditions to the desired product. The conditions for this hydrolysis are much milder than anticipated, only requiring dilute aqueous mineral acid, such as dilute sulfuric acid, hydrochloric acid, or a sulfonic acid. The amount of acid is at least about 1 mol/mol 1 (after that necessary for neutralization of 2). Generally the reaction is conducted between about 20° C. and about 80° C. for a time between about one and about 24 hours until the reaction is substantially complete. Preferably the reaction is conducted at about 50° C. for about four hours. This contrasts with the conditions required to hydrolyze an acetamide, which usually require extended reflux with concentrated acid.

EXAMPLES

Example 1: Preparation of O-(E-3-chloro-2-propenyl) hydroxamate sodium salt

Hydroxylamine sulfate (10.67 g; 0.065 mol; 1.3 equiv) and water (20 g) were combined in a 300-mL 3-necked flask equipped with an addition funnel. The mixture was cooled to 5° C. and 50% sodium hydroxide (10.4 g; 0.13 mol; 1.3 equiv) was added rapidly dropwise over about 15 seconds such that the temperature of the solution remained below 35° C. The reaction mixture was cooled to 10° C. and acetic anhydride (13.27 g; 0.13 mmol; 1.3 equiv) was added dropwise over about 1 minute such that the temperature did not exceed 40° C. The resulting white slurry was cooled to below 10° C. and 50% sodium hydroxide (19.6 g; 0.245 mmol; 2.45 equiv) was added over about 2 minutes such that the temperature of the reaction mixture did not exceed 50° C. To the resulting solution was added E-1,3-dichloropropene (11.10 g; 0.100 mol) and the mixture was heated to 65° C. for 3 hours to consume >99% of the dichloropropene as indicated by GC analysis. The reaction mixture was cooled to room temperature and water (36 mL) was added with thorough mixing. After allowing 15 min for settling, two discrete layers were observed. The bottom organic layer was collected. The remaining aqueous solution was extracted with ethyl acetate (1×10 mL), and this extract was combined with the initial organic solution. This solution of 1 was diluted with toluene (10 mL). A precooled (5° C.) mixture of 50% sodium hydroxide (8.0 g; 0.10 mol; 1.0 equiv) and water (8 mL) were added and the layers were thoroughly mixed. The layers were allowed to settle for 5 minutes and the lower aqueous solution of 2 (the sodium salt of 1) was removed and used as is. The upper organic layer containing impurities and <1% 1 (GC analysis) was discarded. $^1$H NMR (CDCl3) d 8.7 (br s, 1H), 6.348 (d, 1H J=13.40 Hz), 6.082 (td, 1H, J=7.14, 13.43 Hz), 4.36 (br s 2H), 1.931 (br s, 3 H). FDMS (m/e): 149 (M$^+$).

Example 2: Acetyl Exchange to afford O-E-3-Chloro-2 propenylhydroxylamine Hydrochloride (3·HCl) with Acety Recycling The aqueous solution of 2 from a 0.25 mol reaction was added over 1 minute to a mixture of hydroxylamine sulfate (26.7 g; 0.163 mol; 1.3 equiv) and 25 mL of water precooled to 5° C. Aliquat 336 (1.14 mL; 0.0025 mmol; 0.01 equiv was added and the reaction mixture was heated to 65° C. for 8 hours to afford 79% conversion to the desired product. The reaction mixture was cooled to room temperature and the layers were allowed to separate. The aqueous laye (containing acetohydroxamic acid and hydroxylamine) wa removed and set aside for potential recycling. The organi solution was washed with water (5 mL), diluted with toluen (25 mL) and then extracted with a mixture of 14 mL conc HCl (11.6M; 0.162 mol) and water (14 mL). The layers wer allowed to settle and the bottom aqueous layer containing the hydrochloride salt of 3 was removed. This was washed with two 10 mL portions of toluene to afford 49.0 g of aqueous 3·HCl. Titration of this material indicated 3.9% HCl and 37.7% 3·HCl. This translates to 18.4 g of 3·HCl for an overall 51% yield based on 1,3-dichloropropene as the limiting reagent. $^1$H NMR (DMSO-d6) of 40% aq 3·HCl: d 6.746 (d, 1H, J=13.23 Hz), 6.134 (td, 1H, J=7.29, 13.18 Hz), 4.555 (d, 2H, J=7.07 Hz). $^1$H NMR (CDCl$_3$) of 3: d 6.277 (dd, 1H, J=1.53, 13.55 Hz), 6.057 (td, 1H, J=6.78, 13.37 Hz), 5.429 (br s, 2H), 4.138 (d, 2H, J=6.65 Hz).

Example 3: Acidic Hydrolysis to Afford O-E-3-Chloro-2-propenylhydroxylamine Hydrochloride (3·HCl)

The aqueous solution of 2 from a 0.10 mol reaction was cooled to 5° C. Sulfuric acid (10.7 mL; 0.20 mol; 2.0 equiv) was added dropwise such that the temperature remained below 35° C. The reaction mixture was heated to 50° C. for 4 hours to completely consume 1 as determined by GC analysis. The reaction mixture was cooled to 5° C., and 50% sodium hydroxide (35.2 g; 0.44 mol; 4.4 equiv) was added over 10 minutes such that the temperature remained below 40° C. Toluene (15 mL) was then added, the mixture was thoroughly shaken, and the two layers along with some precipitate were allowed to settle for 15 minutes. The precipitate and the lower aqueous layer were removed and discarded. The upper organic layer was extracted with a cold (5° C.) mixture of concentrated HCl (8 mL) and water (8 mL) to afford an aqueous solution of 3·HCl. The upper organic layer was extracted with an additional 1 mL of water and then discarded, and the combined aqueous solution of 3·HCl was analyzed by GC and $^1$H NMR. Titration of 0.6501 g of this solution indicated 1.7% HCl and 31.9% 3·HCl. This translated to 9.53 g (66%) of 3·HCl.

We claim:

1. A method comprising the steps of:

a) forming in an aqueous solution a hydroxamic acid from a hydroxylamine free base and anhydride having the formula (RCO)$_2$O wherein R is H or a substituted or unsubstituted C$_{2-6}$ alkyl, C$_{2-6}$ alkenyl, C$_{6-10}$ aryl, or C$_{4-10}$ heteroaryl; and, without isolation, b) treating said hydroxamic acid with an alkylating agent in the presence of at least one proton scavenger under conditions sufficient to consume substantially all of said alkylating agent to form O-substituted hydroxamate wherein the solvent used for the aqueous solution of steps (a) and (b) is water without a co-solvent.

2. The method of claim 1 wherein said alkylating agent is selected from the group consisting of primary, allylic or benzylic halides or sulfonates and mixtures thereof.

3. The method of claim 1 wherein said proton scavenger is selected from the group consisting of alkali and alkaline earth metal hydroxides, alkoxides, carbonates and mixtures thereof.

4. The method of claim 1 wherein said consuming conditions comprise temperatures between about 40° C. and about 100° C. and processing times between about 1 hour and about 12 hours.

5. The method of claim 1 further comprising the step of purifying said O-substituted hydroxamate as its salt by extraction into caustic.

6. The method of claim 5 wherein said caustic is an aqueous solution having a pH of at least about 12.

7. The method of claim 1 further comprising removing the acyl protecting group by reacting said hydroxamate with hydroxylamine free base under conditions sufficient to product hydroxyamic acid and free base of O-substituted hydroxylamine.

8. The method of claim 1 further comprising the step of hydrolyzing said O-(substituted)hydroxamate under acidic conditions sufficient to produce O-substituted hydroxylamine.

9. The method of claim 8 wherein said acidic conditions comprise treatment with at least about 1 equivalent of a mineral or sulfonic acid in aqueous solution at a temperature between about 20° C. to about 80° C. for between about 1 and about 24 hours.

* * * * *